(12) United States Patent
Neal et al.

(10) Patent No.: US 7,980,699 B2
(45) Date of Patent: Jul. 19, 2011

(54) METHOD FOR REGISTERING MULTIPLE DATA SETS

(75) Inventors: Daniel R. Neal, Tijeras, NM (US); Leander Zickler, Mountain View, CA (US)

(73) Assignee: AMO Wavefront Sciences, LLC., Santa Ana, CA (US)

( * ) Notice: Subject to any disclaimer, the term of this patent is extended or adjusted under 35 U.S.C. 154(b) by 0 days.

(21) Appl. No.: 12/418,841

(22) Filed: Apr. 6, 2009

(65) Prior Publication Data

US 2009/0316112 A1    Dec. 24, 2009

Related U.S. Application Data

(60) Provisional application No. 61/042,630, filed on Apr. 4, 2008.

(51) Int. Cl.
*A61B 3/00* (2006.01)
*A61B 3/10* (2006.01)

(52) U.S. Cl. ......... 351/246; 351/205; 351/206; 351/212

(58) Field of Classification Search .................. 351/205, 351/246, 206, 212
See application file for complete search history.

(56) References Cited

U.S. PATENT DOCUMENTS

| | | | |
|---|---|---|---|
| 4,540,254 A | 9/1985 | Humphrey | |
| 4,761,071 A | 8/1988 | Baron | |
| 4,995,716 A | 2/1991 | Warnicki et al. | |
| 5,406,342 A | 4/1995 | Franciscus | |
| 5,491,524 A | 2/1996 | Hellmuth et al. | |
| 6,116,738 A | 9/2000 | Rorabaugh et al. | |
| 6,396,069 B1 | 5/2002 | MacPherson et al. | |
| 7,044,602 B2 | 5/2006 | Chernyak | |
| 2003/0086057 A1 | 5/2003 | Cleveland | |
| 2004/0143246 A1 | 7/2004 | Maeda et al. | |
| 2004/0263785 A1 | 12/2004 | Chernyak | |
| 2006/0215113 A1 | 9/2006 | Chernyak | |

FOREIGN PATENT DOCUMENTS

| | | |
|---|---|---|
| AU | 2006200896 A1 | 3/2006 |
| EP | 1316287 A2 | 4/2003 |
| EP | 1985269 A1 | 10/2008 |

*Primary Examiner* — Jack Dinh

(57) ABSTRACT

Devices, systems, and methods that facilitate optical analysis, particularly for the diagnosis and treatment of refractive errors of the eye. Embodiments of the invention may facilitate the use of multi-modal diagnostic instruments and instrument systems, making it easier to acquire and fuse data from different measurements of the eye. For example, wavefront aberrometry may be fused with corneal topography, optical coherence topography and wavefront, optical coherence topography and topography, pachymetry and wavefront, etc. While some of these different optical datasets may be obtained simultaneously, it is often difficult and/or disadvantageous to attempt to acquire the images or other data at exactly the same time. Advantageously, both patient movement between measurements (and/or during a measurement sequence) can be identified, as well as changes in the eye itself (including those induced by the measurement, such as changes in the size of the pupil, changes in pupil location, etc.).

16 Claims, 6 Drawing Sheets

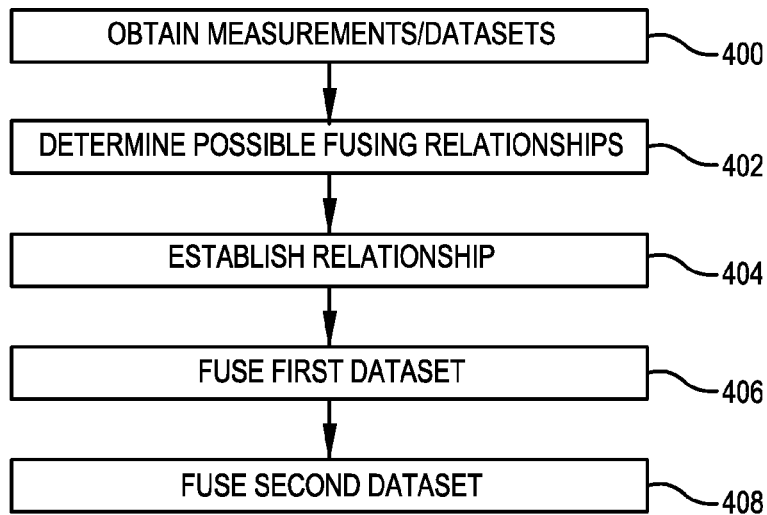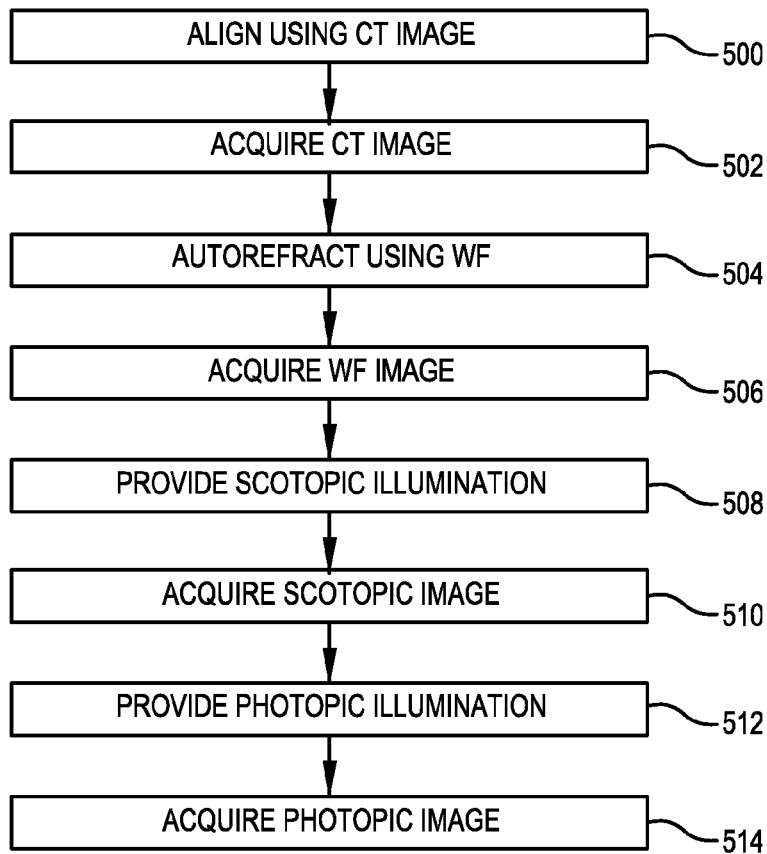

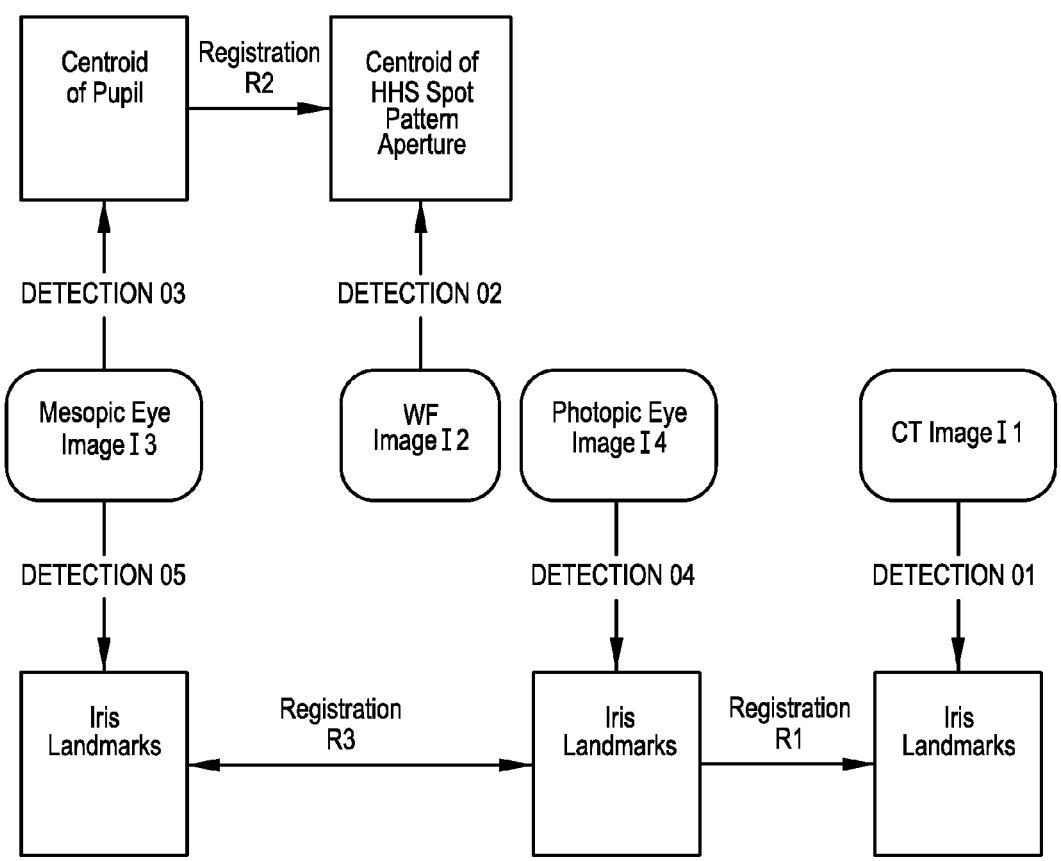

METHOD FOR REGISTERING MULTIPLE DATA SETS

CROSS-REFERENCES TO RELATED APPLICATIONS

This application claims the benefit of provisional application No. 61/042,630, filed on Apr. 4, 2008, the full disclosure of which is incorporated herein by reference.

BACKGROUND

The present application relates generally to registering multiple datasets with each other. In an exemplary embodiment, the present invention relates to registering differing ophthalmic datasets from different measurements (such as a wavefront measurement and a corneal topography map) of an eye.

Known laser eye procedures generally employ an ultraviolet or infrared laser to remove a microscopic layer of stromal tissue from the cornea of the eye to alter the refractive characteristics of the eye. The laser removes a selected shape of the corneal tissue, often to correct refractive errors of the eye. Ultraviolet laser ablation results in photo-decomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of a pattern of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, thermal shaping, and the like.

Known corneal correction treatment methods have generally been successful in correcting standard vision errors, such as myopia, hyperopia, astigmatism, and the like. However, as with all successes, still further improvements would be desirable. Toward that end, wavefront measurement instruments are now available to measure the refractive characteristics of a particular patient's eye.

One promising wavefront measurement system is the iDESIGN ADVANCED WAVESCAN STUDIO System, which includes a Hartmann-Shack wavefront sensor assembly that may quantify higher-order aberrations throughout the entire optical system, including first and second-order sphero-cylindrical errors and third through sixth-order aberrations caused by coma and spherical aberrations. With advanced algorithms for measuring and applying the wavefront correction (e.g. Fourier or zonal), even higher spatial frequency structures can be corrected, providing that adequate registration can be maintained between the intended correction and its application in a practical system. The wavefront measurement of the eye creates a high order aberration map that permits assessment of aberrations throughout the optical pathway of the eye, e.g., both internal aberrations and aberrations on the corneal surface. Thereafter, the wavefront aberration information may be saved and thereafter input into a computer system to compute a custom ablation pattern to correct the aberrations in the patient's eye. A variety of alternative wavefront or other aberration measurement systems may also be available Customized refractive corrections of the eye may take a variety of different forms. For example, lenses may be implanted into the eye, with the lenses being customized to correct refractive errors of a particular patient. By customizing an ablation pattern or other refractive prescription based on wavefront measurements, it may be possible to correct minor refractive errors so as to reliably and repeatably provide visual acuities better than 20/20. Alternatively, it may be desirable to correct aberrations of the eye that reduce visual acuity, even where the corrected acuity remains less than 20/20.

While wavefront measurement systems have been highly successful, improvements are still possible. For example, in some instances it may be desirable to concurrently diagnose the refractive errors of the eye using two or more different optical measurements so as to provide a better diagnosis (and treatment) of the refractive errors in the optical tissues of the eye. For example, the iDESIGN ADVANCED WAVESCAN STUDIO System includes both a wavefront aberrometer and corneal topographer. In order to fully take advantage of two different data sources for corneal treatment planning, however, it will generally be desirable to combine the data from the two optical measurement instruments.

Consequently, what is needed are methods, systems and software for registering datasets from separate optical measurement devices.

Multi-modal diagnostic instruments are being developed that acquire data from different measurements of the eye. For example, a multi-modal diagnostic instrument may include, for example, wavefront aberrometry and corneal topography (CT), optical coherence topography (OCT) and wavefront (WF), optical coherence topography and topography, pachymetry and wavefront, and so forth. The different measurements taken by these multi-modal diagnostic instruments may be more useful if are be registered together. Often it is difficult to acquire the images at exactly the same time, which requires synchronized cameras. Accordingly, it would be useful to provide systems and methods that allow image data to be registered that was taken by different devices, or the same device, at different times.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention generally provides devices, systems, and methods that facilitate optical analysis, particularly for the diagnosis and treatment of refractive errors of the eye. Embodiments of the invention may facilitate the use of multi-modal diagnostic instruments and instrument systems, making it easier to register, align, or fuse data from different measurements of the eye. For example, wavefront aberrometry may be fused with corneal topography, optical coherence topography with wavefront, optical coherence topography with topography, pachymetry with wavefront, etc. While some of these different optical datasets may be obtained simultaneously, it may be difficult and/or disadvantageous to attempt to acquire the images or other data at exactly the same time. Advantageously, in accordance with embodiments herein, both patient movement between measurements (and/or during a measurement sequence) can be identified, as well as changes in the eye itself (including those induced by the measurement, such as changes in the size of the pupil, changes in pupil location, etc.).

Improved refractive analysis and refractive treatments may optionally be provided by indirectly registering at least one optical measurement of the eye. For example, an exemplary embodiment includes obtaining images of anterior structures of the eye while the pupil is relatively enlarged (e.g., under scotopic or mesopic conditions) and while the pupil is relatively small (such as a photopic image). These images can then be used to identify a relationship between the pupil size and a location of the pupil relative to a robust landmark of the eye such as an outer iris boundary. The pupil size and location may be determined from wavefront measurements and/or other aberration measurement data as apertured by the iris of the eye. This may help the system to determine an outer iris boundary location from the wavefront measurement using the relationship. An image or images used for exemplary dot grid topography measurements may, along with having the topography data, also include sufficient information regarding the outer iris boundary location relative to the corneal shape to facilitate registration with the wavefront data, and may also include at least an outer portion of the iris image so as to facilitate torsional registration between the topography dataset and the anterior eye photos.

For a fuller understanding of the nature and advantages of the present invention, reference should be made to the ensuing detailed description and accompanying drawings.

BRIEF DESCRIPTION OF THE DRAWINGS

FIG. 4 is a flow chart showing steps for aligning, registering, or fusing data in accordance with an embodiment FIG. 5 is a flow chart showing a measurement sequence that may be used to acquire eye measurements with first and second measuring instruments in accordance with an embodiment.

FIG. 13 is a flow chart schematically illustrating a method of indirectly registering optical datasets of an eye.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order to not obscure the embodiment being described.

Embodiments herein provide devices, systems, and methods that facilitate optical analysis, particularly for the diagnosis and treatment of refractive errors of the eye. Embodiments of the invention facilitate the use of multi-modal diagnostic instruments and instrument systems, making it easier to acquire and fuse (e.g., synthesize) data from different measurements of the eye. For example, wavefront aberrometry may be fused with corneal topography, optical coherence topography and wavefront, optical coherence topography and topography, pachymetry and wavefront, etc. While some of these different optical datasets may be obtained simultaneously, it is often difficult and/or disadvantageous to attempt to acquire the images or other data at exactly the same time. Embodiments herein permit registration of multiple datasets from measurements, regardless of the sequence the measurements were taken.

Acquiring and fusing data from different measurements of the eye has significant potential advantages. For example, wavefront aberrometry and corneal topography may be used separately to each provide a beneficial refractive prescription, but the registration and combination of information from both measurements may provide improved refractive prescriptions and the like. These prescriptions may be used, for example, with a laser surgery system.

Figure 1:
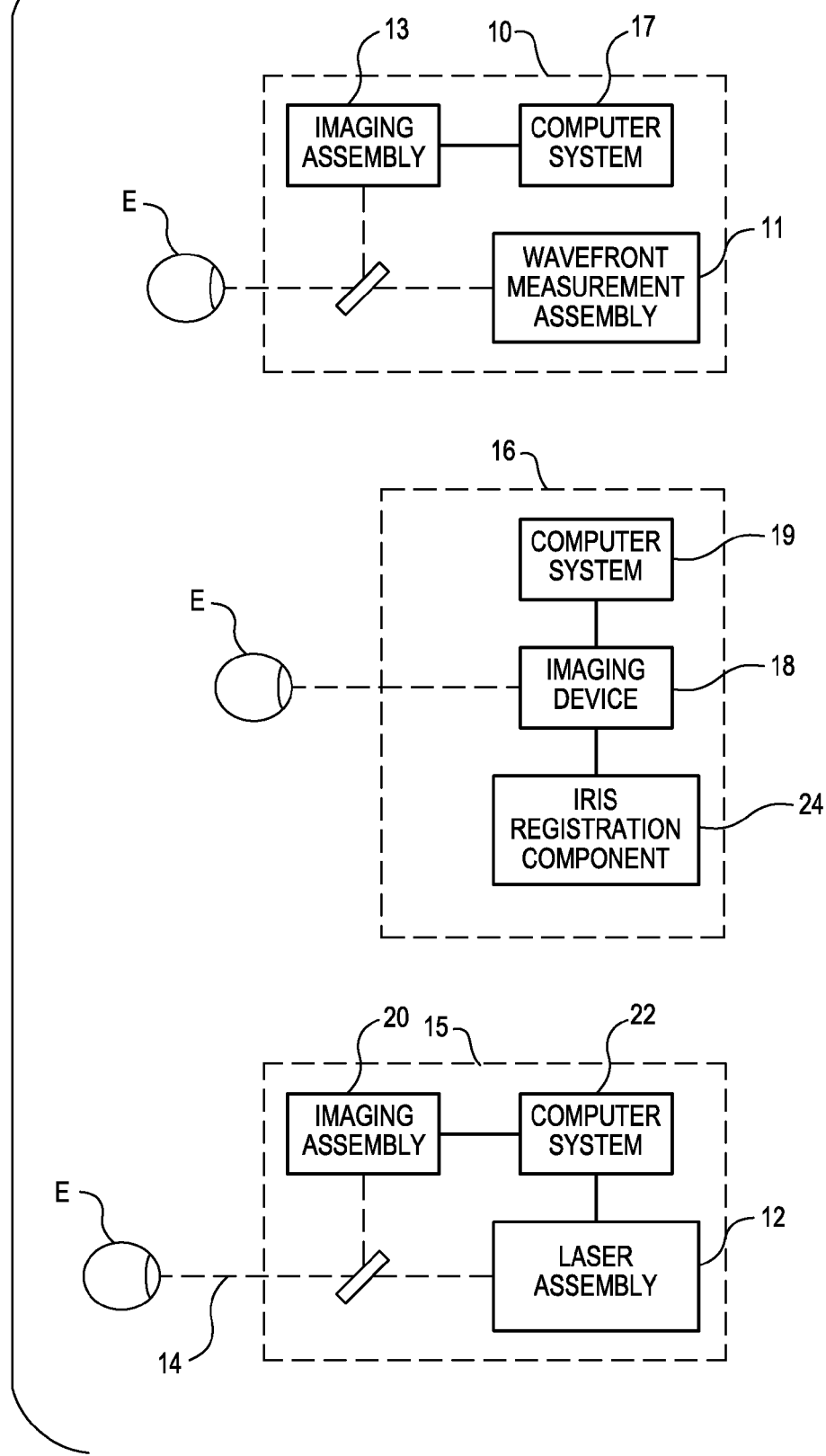
FIG. 1 schematically illustrates a simplified system of one embodiment of the present invention.

FIG. 1 schematically illustrates a simplified system of one embodiment of the present invention. Advantageously, elements, components, subsystems, and method elements to be used in embodiments of the present invention can be taken and/or derived from a number of known structures and methods. Exemplary constituent elements may include structures and/or techniques found in or derived from those of U.S. Pat. No. 7,044,602 in the name of Chernyak and entitled "Methods and Systems for Tracking a Torsional Orientation and Position of an Eye"; US Patent Application Publication No. 2004/0263785 in the name of Chernyak and entitled "Methods and Devices for Registering Optical Measurement Datasets of an Optical System"; and/or US Patent Application Publication No. 2006/0215113 in the name of Chernyak and entitled "Pupilometer for Pupil Center Drift and Pupil Size Measurements at Differing Viewing Distances"; the full disclosures of which are incorporated herein by reference. Alternative embodiments may use, for example, different commercially available pupil location and/or size measurement structures, different iris or other natural or artificial rotational markers, or the like, so that not all aspects of the present invention will necessarily be limited to these particular components.

In the embodiment shown in FIG. 1, the system includes a first measurement instrument 10, a second measurement instrument 16, and a laser system 15. In an embodiment, the first measurement instrument 10 is a wavefront measurement device 10 that measures aberrations and other optical characteristics of an ocular or other optical tissue system. The data from such a wavefront measurement device may be used to generate an optical surface from an array of optical gradients. It should be understood that the optical surface need not precisely match an actual tissue surface, as the gradients will show the effects of aberrations which are actually located throughout the ocular tissue system. Nonetheless, corrections imposed on an optical tissue surface so as to correct the aberrations derived from the gradients should correct the optical tissue system. As used herein terms such as "an optical tissue surface" may encompass a theoretical tissue surface (derived, for example, from wavefront sensor data), an actual tissue surface, and/or a tissue surface formed for purposes of treatment (for example, by incising corneal tissues so as to allow a flap of the corneal epithelium to be displaced and expose the underlying stroma during a LASIK procedure).

The second measurement instrument 16 may include a corneal topographer. Corneal topographer 16 may be used to diagnose and examine the corneal surface. Corneal topographer 16 typically includes an imaging device 18, such as a frame grabber that takes images of the cornea. The images obtained by the frame grabber are analyzed by a computer system 19, and the computer system may generate one or more graphical and/or tabular outputs, including three dimensional topographical maps. Corneal topographer 16 may determine the contours of the corneal surface by measuring the elevations and depressions in the corneal surface. One example of a corneal topographer 16 utilizes a laser, LED or other light source that maps a series of dots on the surface of the cornea. Reflected light rays of the dots are reflected to a sensor, which in turn provides data to the computer system 19 regarding the reflected dots. The computer system 19 forms a corneal elevation map from the data. An example of such a system, sometimes called a full gradient topographer, is the iDESIGN ADVANCED WAVESCAN STUDIO System, which is at least partially described in co-pending U.S. patent application Ser. No. 12/347,909, filed Dec. 31, 2008, and entitled "Systems and Methods for Measuring the Shape and Location of an Object," and which is herein incorporated by reference.

Another example of a corneal topographer is the HUMPHREY ATLAS Corneal Topographer, from Zeiss Humphrey Systems, of Dublin, Calif., which is an instrument that uses Placido disk technology to generate images of the corneal surface. The ring-based corneal topographer 16 may be based on a method that captures the reflection of rings of light off of the surface of the cornea and measures the distortion in the reflected light. A detector (not shown) captures the reflected images and computer system 19 processes the data, and displays the information in one or more formats selected by the user. For example, corneal topographer 16 may provide an axial map (which describe the radius of the curvature of the cornea relative to optic axis), curvature maps (which portray the radius of the curvature independent of the optic axis), and/or elevation maps (which illustrate the radius relative to a reference sphere).

As can be appreciated, the full gradient topographer and the HUMPHREY ATLAS topographer are merely two examples of corneal topographers that may be used with the present invention. Other corneal topographers sold by Topcon Medical Systems, Dicon Diagnostics, Haag-Streit, EyeQuip, Tomey Corp., Bausch & Lomb, Carl Zeiss Ophthalmic Systems, Nidek, and Laser Sight may be used with the present invention. Some systems and methods for measuring a corneal topography of an eye are described in U.S. Pat. Nos. 4,761,071, 4,995,716, 5,406,342, 6,396,069, 6,116,738, 4,540,254 and 5,491,524, the full disclosures of which are incorporated herein by reference.

In an embodiment, the corneal topographer 16 includes an iris registration component, which may include cameras and pupilometer measurement features, such as described in US Patent Application Publication No. 2006/0215113 in the name of Chernyak and entitled "Pupilometer for Pupil Center Drift and Pupil Size Measurements at Differing Viewing Distances," the full disclosure of which is incorporated herein by reference. The iris registration features may alternatively be included with the first measurement instrument 10, or as a completely separate system. In addition, although shown as two separate measurement instruments 10 and 16, the features of the first and second measurement instruments may be provided on a single system.

Furthermore, while embodiments herein focus on registering datasets of an eye from a wavefront measurement instrument, such as the first measurement instrument 10, and a corneal topographer, such as the second measurement instrument 16, embodiments of the present invention are equally applicable to registering datasets obtained by a variety of other optical measurement instruments. For example, the present invention may be used to fuse data from optical coherence topography and wavefront, optical coherence topography and topography, pachymetry and wavefront, and the like.

The laser surgery system 15 surgery system 15 includes a laser assembly 12 that produces a laser beam 14. Laser assembly 12 is optically coupled to laser delivery optics (not shown), which directs laser beam 14 to an eye E of a patient. An imaging assembly 20, such as a microscope is mounted on the delivery optics support structure to image a cornea of eye E during the laser procedure.

Laser assembly 12 generally comprises an excimer laser source, typically comprising an argon-fluorine laser producing pulses of laser light having a wavelength of approximately 193 nm. Laser assembly 12 will preferably be designed to provide a feedback stabilized fluence at the patient's eye, delivered via delivery optics. Although an excimer laser is the illustrative source of an ablating beam, other lasers may be used.

Laser assembly 12 and delivery optics will generally direct laser beam 14 to the eye E under the direction of a computer system 22. Computer system 22 will generally selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system will be under computer control of computer system 22 to affect the desired laser sculpting process so as to deliver the customized ablation profile, with the computer system ideally altering the ablation procedure in response to inputs from the optical feedback system. The feedback will preferably be input into computer system 22 from an automated image analysis system, or may be manually input into the processor by a system operator using an input device in response to a visual inspection of analysis images provided by the optical feedback system. Computer system 22 will often continue and/or terminate a sculpting treatment in response to the feedback, and may optionally also modify the planned sculpting based at least in part on the feedback.

While embodiments herein are described primarily in the context of improving diagnosis and treatment of the refractive errors of the eye using a laser eye surgery system 15, it should be understood the present invention may be adapted for use in alternative diagnosis of other optical systems, eye treatment procedures, and optical systems such as femtosecond lasers and laser treatment, infrared lasers and laser treatments, radial keratotomy (RK), scleral bands, follow up diagnostic procedures, and the like.

Figure 2:
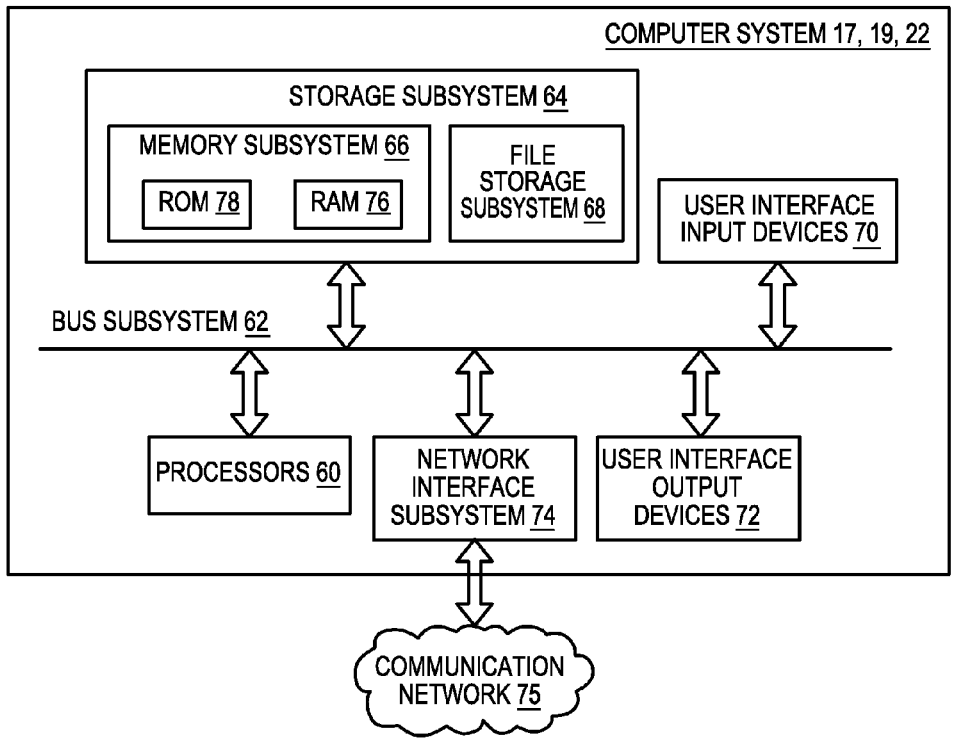
FIG. 2 is a simplified block diagram of an exemplary computer system in accordance with an embodiment.

FIG. 2 is a simplified block diagram of an exemplary computer system 17, 19, 22 in accordance with an embodiment. The computer system typically includes at least one processor 60 which communicates with a number of peripheral devices via a bus subsystem 62. These peripheral devices may include a storage subsystem 64, comprising a memory subsystem 66 and a file storage subsystem 68, user interface input devices 70, user interface output devices 72, and a network interface subsystem 74. Network interface subsystem 74 provides an interface to a communication network 75 for communication with other imaging devices, databases, or the like.

The processor 60 performs the operation of the computer systems 17, 19, 22 using execution instructions stored in the memory subsystem 66 in conjunction with any data input from an operator. Such data can, for example, be input through user interface input devices 70, such as the graphical user interface. Thus, processor 60 can include an execution area into which execution instructions are loaded from memory. These execution instructions will then cause processor 60 to send commands to the computer system 17, 19, 22, which in turn control the operation of the first measurement instrument 10, the second measurement instrument 16, and the laser system 15. Although described as a "processor" in this disclosure and throughout the claims, the functions of the processor may be performed by multiple processors in one computer or distributed over several computers.

User interface input devices 70 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. In general, use of the term "input device" is intended to include a variety of conventional and proprietary devices and ways to input information into the computer system. Such input devices will often be used to download a computer executable code from a computer network or a tangible storage media embodying steps or programming instructions for any of the methods of the present invention.

User interface output devices 72 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide non-visual display such as via audio output devices. In general, use of the term "output device" is intended to include a variety of conventional and proprietary devices and ways to output information from the computer system to a user.

Storage subsystem 64 stores the basic programming and data constructs that provide the functionality of the various embodiments. For example, database and modules implementing the functionality of embodiments described herein may be stored in storage subsystem 64. These software modules are generally executed by processor 60. In a distributed environment, the software modules may be stored in a memory of a plurality of computer systems and executed by processors of the plurality of computer systems. Storage subsystem 64 typically comprises memory subsystem 66 and file storage subsystem 68.

Memory subsystem 66 typically includes a number of memories including a main random access memory (RAM) 76 for storage of instructions and data during program execution and a read only memory (ROM) 78 in which fixed instructions are stored. File storage subsystem 68 provides persistent (non-volatile) storage for program and data files, and may include a hard disk drive, a floppy disk drive along with associated removable media, a Compact Digital Read Only Memory (CD-ROM) drive, an optical drive, DVD, CD-R, CD-RW, or removable media cartridges or disks. One or more of the drives may be located at remote locations on other connected computers at other sites coupled to the computer system. The databases and modules implementing the functionality of the present invention may also be stored by file storage subsystem 68.

Bus subsystem 62 provides a mechanism for letting the various components and subsystems of the computer system communicate with each other as intended. The various subsystems and components of the computer system need not be at the same physical location but may be distributed at various locations within a distributed network. Although bus subsystem 62 is shown schematically as a single bus, alternate embodiments of the bus subsystem may utilize multiple busses.

The computer system itself can be of varying types including a personal computer, a portable computer, a workstation, a computer terminal, a network computer, a module in the imaging unit, a mainframe, or any other data processing system. Due to the ever-changing nature of computers and networks, the description of the computer system depicted in FIG. 2 is intended only as a specific example for purposes of illustrating one embodiment of the present invention. Many other configurations of the computer system are possible having more or less components than the computer system depicted in FIG. 2.

Figure 3:
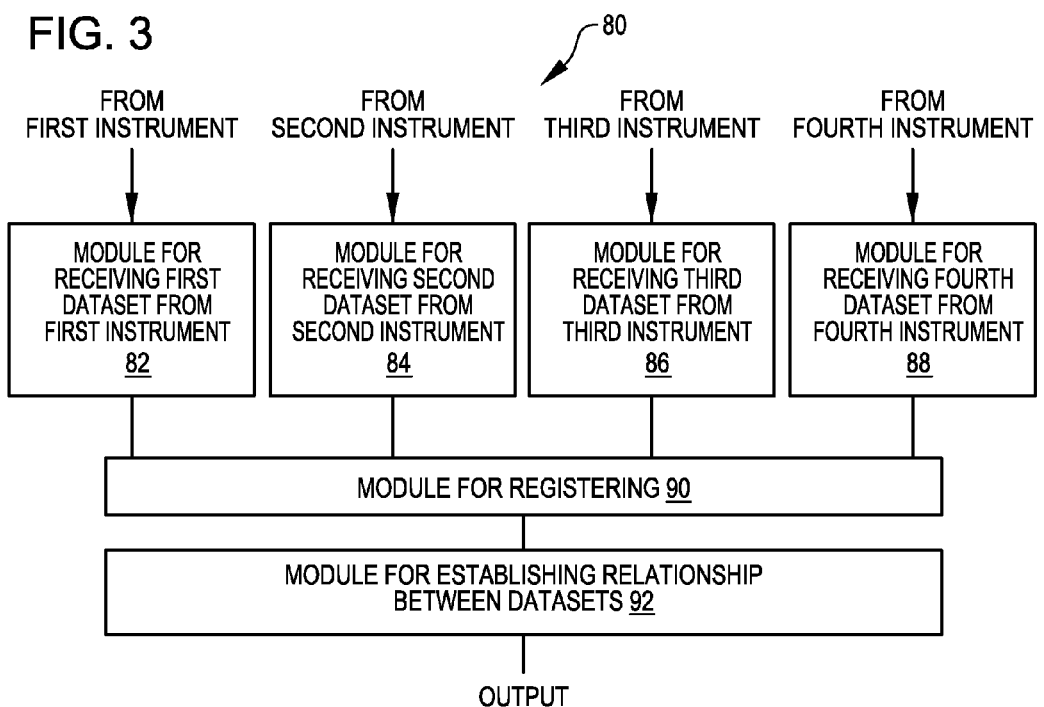
FIG. 3 schematically illustrates a plurality of modules that may carry out embodiments of the present invention.

FIG. 3 schematically illustrates a plurality of modules 80 that may carry out embodiments of the present invention. The modules 80 may be software modules, hardware modules, or a combination thereof. If the modules are software modules, the modules will be embodied on a computer readable medium and processed by a processor 60 in any of computer systems of the present invention.

A first dataset from a first instrument will be received by module 82. The first dataset is typically an optical measurement and/or image of an optical system, such as an eye. For example, in one embodiment, the optical measurement is in the form of a wavefront measurement of a patient's eye. Such a wavefront measurement may be obtained by the wavefront measurement assembly 11.

A second dataset from a second instrument is received by module 84. The second dataset is also typically an optical measurement and/or image of the same optical system. For example, in one embodiment, the second optical measurement is in the form of a corneal topographical map of the patient's eye E, from the imaging device 18.

A third and fourth modules 86, 88 receive third and fourth datasets, respectively, which, in an embodiment, are also optical measurements and/or images of an optical system, such as an eye E. As described below, these additional datasets provide information that may be used to fuse the first and second datasets, and/or may provide additional data that may be fused with the first and second datasets. Although the embodiment shown includes the two modules 86, 88, a single module may be used, and a single dataset, depending upon the information utilized to fuse the first and second datasets and/or to be fused with the first and second datasets. In an embodiment, the third dataset is a iris registration scotopic/mesopic image from the iris registration component 24. This image measures the pupil size, position and shape, and the outer iris boundary position and size in low light conditions. In an embodiment, the fourth dataset is an iris registration photopic image from the iris registration component 24. This image is used to measure the pupil size, position and shape, and the outer iris boundary position and size in bright light conditions. These images may be obtained by the iris registration component 24, for example.

The first, second, third and fourth datasets may be transmitted from the first instrument 10 and second instrument 16 over a communication network, or the datasets from each of the devices may be stored on a computer readable medium and uploaded to the computer system that processes the modules 80.

In order to take maximum advantage of the first, second, third and/or fourth datasets for diagnosis of refractive errors of the eye and for corneal treatment planning, the datasets may be registered, or the data from the images fused. Consequently, the first, second, third and fourth datasets may be transmitted to a registration module 90 where one or more image processing algorithms are applied to the datasets to register the datasets.

Some measurement instruments may not produce datasets that are readily registered. Incompatibility may be based upon the fact that the two datasets are taken at different times, and/or movement of the eye may occur between measurements. To address such problems, a single measurement instrument might acquire multiple different types of ophthalmic measurements simultaneously, using synchronized cameras or the like. Although simultaneous recording might facilitate registration, it is often difficult, impossible, or undesirable to acquire the images at exactly the same time. For example, different illumination states may be desired for different types of measurements, requiring measurements be taken at different times. For example, in some ring-based measurement systems, corneal topography (CT) illumination may be incompatible with iris registration imaging via wavefront, because wavefront may benefit from a largest pupil size (thus scotopic), but the corneal topography illumination shrinks the size of the pupil.

In accordance with an embodiment, a relationship module 92 is provided that allows datasets of the eye to be registered, whether taken by a single measurement instrument having a single eye measurement location, or by separate measurement devices or the like having separate eye measurement locations. Moreover, in accordance with an embodiment, the multiple measurements may be taken at different moments in time, and the measurements may be registered together despite movement of the eye between the eye measurements. Thus, embodiments described herein may significantly facilitate use of the combination of some eye measurement systems not typically combinable for simultaneous measurement, and thus enhance measurement accuracy.

As described in more detail below, the relationship module 92 determines proper registration and alignment between multiple data types so that these data may be used together (fused) to produce a combined measurement. In embodiments, the relationship module 92 removes limitations of measurement sequence and illumination in the registration process. In accordance with one embodiment, as further described below, the relationship module 92 identifies, and corrects for, changes in the pupil size, position and shape during the measurement process, and thereby maintains accurate alignment between the various measurements.

FIG. 4 is a flow chart showing steps for registering or fusing data in accordance with an embodiment. Beginning at step 400, the first and second measuring instruments 10 and 16 are used to acquire measurements of the eye. The measurements include image datasets. A sequence for acquiring measurements is described together with FIG. 5.

FIG. 5 is a flow chart showing a measurement sequence that may be used to acquire eye measurements with the first and second measuring instruments 10, 16 in accordance with an embodiment. Beginning at step 500, the second measuring instrument 16 is aligned using the corneal topography image. At step 502, the corneal topography image is acquired.

At step 504, the first measuring instrument 10 is used to autorefract, for example using the wavefront measurement assembly 11. At step 506, a wavefront image is acquired.

At step 508, illumination is set to take a scotopic image. At step 510, the scotopic image is acquired. At step 512, illumination is set to take a photopic image, and at step 514, after a delay to allow the pupil to contract, the photopic image is acquired.

After the sequence in FIG. 5, the system has four different images. Acquisition of these images does not have to be in the sequence provided in FIG. 5. In addition, the images need not be taken at the same time, and they may have different illumination from image to image. A time difference between measurements may result in the eye moving to a different location and a change in illumination may result in the pupil changing in size and relative position.

Figure 6:
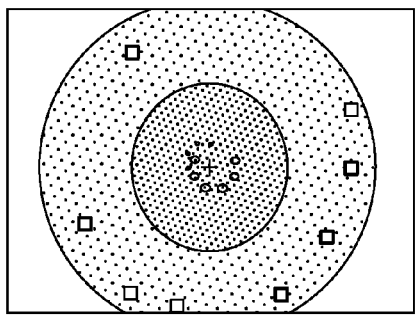
FIGS. 6 to 9 show images taken via the measurement sequence of FIG. 5.
Figure 7:
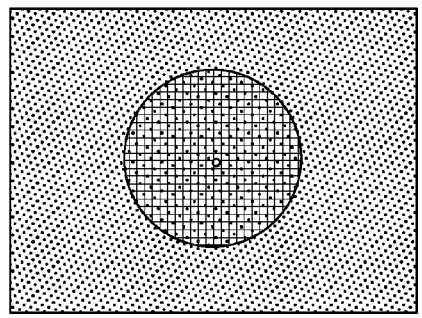
Figure 8:
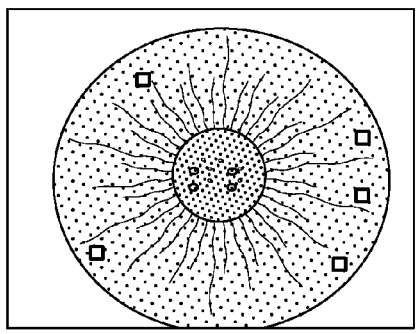
Figure 9:
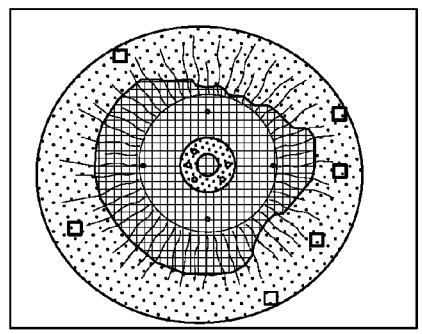

FIGS. 6 to 9 show images taken via the measurement sequence of FIG. 5. FIG. 6 is the iris registration scotopic/mesopic image, which measures the pupil size, position and shape, and the outer iris boundary position and size in low light conditions. The image contains feature detail of the iris. FIG. 7 is the wavefront aberrometer image, which measures light scattered or reflected from a point on the retina. FIG. 8 is the iris registration photopic image, which measures the pupil size, position and shape, and the outer iris boundary position and size in bright light conditions. The image contains feature detail of the iris. FIG. 9 is the corneal topography image.

Returning now to FIG. 4, after the measurements are obtained in step 400, at step 402, possible data fusion relationships are evaluated. These data fusion relationships are data types that are available to multiple images, so that registration between the multiple images may be made by using the commonly available data types. Preferably, a characteristic common to all images is used for data fusion.

In some embodiments, the data may be fused by adjusting data location and orientation. Alternative embodiments may be fused by adjusting data location and limiting eye rotation about the optical axis, often by avoiding gross movement of the patient between measurements (such as by using a common eye measurement location) and by limiting the time between data acquisition for the different measurements. Fortunately, the time sequence for taking multiple measurements on an exemplary multi-modal system may be short, with total image acquisition time for obtaining a plurality of different types of measurements optionally taking less than 30 seconds, often less than 10 seconds, preferably less than 5 seconds, and in some cases taking about 4 seconds or less than a second. Even images/measurements taken with illumination sufficiently different to alter a size of the pupil may be taken at times that are quite close, the differences between the image acquisition times for wavefront and corneal topography, for example, typically being within 1 second, and in exemplary embodiments being within $\frac{1}{5}$ of a second, $\frac{1}{10}$ of a second, or $\frac{1}{30}$ of a second. Under such conditions, rotation of the eye between measurements may be negligible.

In embodiments, rotational adjustments between datasets may be identified using simultaneous pupil shape information (such as may be available from the wavefront data), simultaneous retinal data (optionally including images of vessels or other landmarks obtained during wavefront data acquisition), simultaneous iris data obtained from an co-axial or an off-axis camera, or the like.

Figure 10:
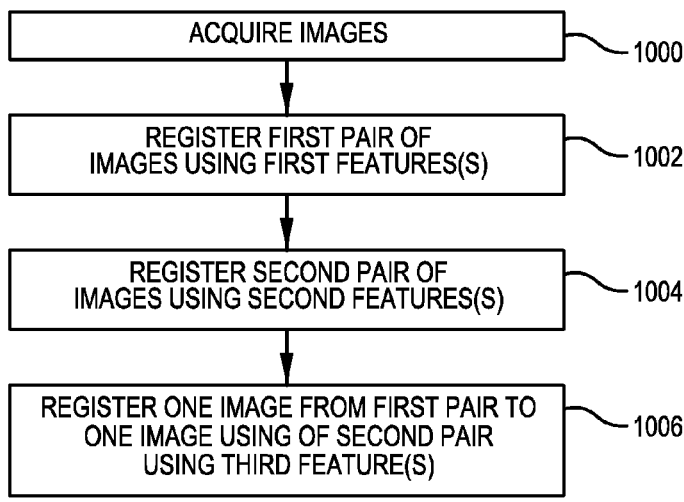
FIG. 10 is a flow chart representing a process for registering multiple datasets that do not have a common characteristic in accordance with an embodiment.

Thus, a number of different systems exist for registration of images to each other when the images have a common characteristic. However, due to the difference measurement principles used to create images, a characteristic common to all images may not be available. It may be sufficient, however, to register images together in subsets, and then register subsets to other subsets until all images are registered to each other. For example, FIG. 10 is a flow chart representing a process for registering multiple datasets that do not have a common characteristic in accordance with an embodiment. At step 1000, the images are acquired. At step 1002, two images are registered with each other using one or more first features, thus creating a first registered image pair. At step 1004, two images, at least one being different from the first set, are registered with each other using one or more second features, thus creating a second registered image pair. At step 1006, the two registered image pairs are registered with each other using one image from each pair and one or more third features different from the first features to register the images. After the process in FIG. 10, all images have a determined spatial relationship with each other.

The process of FIG. 10 works particularly well when two datasets are difficult to register with each other because the two datasets do not include common characteristics. In such a situation, an image or a group of images may act as intermediary datasets for the two datasets that are difficult to register together. For example, for the system shown in FIG. 1, as further described below, the corneal topography image is difficult to register directly to the wavefront image because the two images do not contain any common features. The pupil is visible in the wavefront image as the region illuminated, but it is potentially obscured in the corneal topography image by the array of reflected spots or the reflected Placido rings. Furthermore, the wavefront and corneal topography images are taken under different lighting conditions and may be taken at widely different times (hence the eye may be in a different position). Thus, using the process in FIG. 10, the corneal topography image and the wavefront image may each be separately registered to an intermediary dataset, and through those two separate registrations, are ultimately registered to each other. In other words, the corneal topography image is registered to the intermediary dataset, which in turn is registered to the wavefront image. In such a system, the two images that are registered at step 1002 include the corneal topography image and the intermediary dataset, and the two images that are registered at step 1004 are the wavefront image and the intermediary dataset.

Thus, returning to FIG. 4, a relationship is established at step 404, such as the use of the intermediary dataset described above. At step 406, the first dataset is fused using the relationship, and at step 408, the second dataset is fused using the relationship. After the steps in FIG. 4, all images are fused.

Data that is available from the images differs based upon the image type. With image recognition techniques it is possible to find the position and extent of various features in an image. Turning now to the specific four images captured in FIG. 5, for the iris registration images, features that are available include the position, size and shape of the pupil, the position, size and shape of the outer iris boundary (OIB), salient iris features (landmarks) and other features as are determined to be needed.

In the iris registration images, it is possible, without interference from any of the various reflections (iris illumination sources) to find the pupil position, size and shape accurately. This is facilitated by arrangement of the system components such that the illumination sources are near the optical axis, and thus the reflections are near the center of the pupil, and thus do not interfere with finding the pupil's edge. Information from different landmarks may be correlated, for example, by accurately locating the outer iris boundary and/or iris landmarks relative to the pupil. This may help allow a pupil location to be determined from another image in which the pupil itself is not visible, optionally with greater accuracy than may be provided by relying on an image of the limbus alone (as the limbus may appear as a gradual boundary, rather than having a sharp boundary).

In the corneal topography image, however, it may be advantageous to measure the topography as close to the center as possible. In general the corneal topography projected pattern covers the full pupil, including the center and the edge of the pupil. This pattern may interfere with finding the pupil position, size and shape accurately. Furthermore, the illumination is generally adjusted to optimize the corneal topography image for detecting the reflected pattern. This illumination is not necessarily the same, nor optimized for, the detection of the pupil information. Therefore, it may be desirable to find a different feature in the corneal topography image to use for registration information.

It is noted that the strong curvature of the cornea is such that only a limited coverage of the corneal area is often measurable by corneal topography. Usually this coverage includes the pupil and central area, but often does not extend to the outer iris boundary. Thus no projected pattern may be evident in the images near the outer iris boundary. The visible peripheral portion of the iris image included in the corneal topography image may be used for registration, for example, to help accurately locate the pupil (even if the pupil image is not readily seen), to help identify the torsional orientation of the eye about the optical axis of the eye, and/or the like.

Thus it is possible to register the outer iris boundary information that is found in the corneal topography image with that from the iris registration image. The relative position of these two outer iris boundary measurements can be used to determine the correct relative position of the measurement information. Furthermore, the outer iris boundary is a fixed feature in the eye, and does not change with time, or with measurement type.

However, the wavefront aberrometry image generally has no features that correspond to the outer iris boundary. Thus some other feature will often be used to register this image to other images. In wavefront aberrometer, the pupil is back illuminated by the scattering source on the retina, with the retina aperturing the aberrometry data. Thus, the size, shape, and location of the pupil can be accurately determined. The position of the wavefront pupil can thus be registered to the position of the measured pupil from the iris image.

Thus the wavefront data and the corneal topography data can be separately registered to features on the iris registration image. The iris registration image can be treated as a reference image, and both the wavefront data and the corneal topography data can be registered to coordinates that are centered on this image.

The process of FIG. 10 may be used, therefore, to register the wavefront data to the corneal topography data, using the iris registration image as the intermediary. There remains at least one further difficulty, however. That is that the pupil might change position as a function of size. Since the illumination is in general different between acquisition of the wavefront and the iris images, it may be that the pupil has changed substantially in size between the two acquisitions.

This issue may be addressed by interpolating the size of the pupil in the wavefront data onto information known about the pupil size from the iris registration information so as to arrive at the position of the pupil for the wavefront. Note that there are two iris images that can be acquired. These differ in the illumination that is provided. The scotopic (or mesopic) image is taken with minimum illumination, preferably in the IR or Near IR wavelengths of light so that the eye does not respond to illumination by changing in size or position. It is usually desirable to maximize the pupil size during the wavefront and scotopic image acquisition.

The other image is the photopic image. It is acquired by first turning on a bright visible (e.g., green) source of illumination, waiting for the eye to respond, and then acquiring an iris image. This results in an image where the pupil is smaller than that of the scotopic image.

Figure 11:
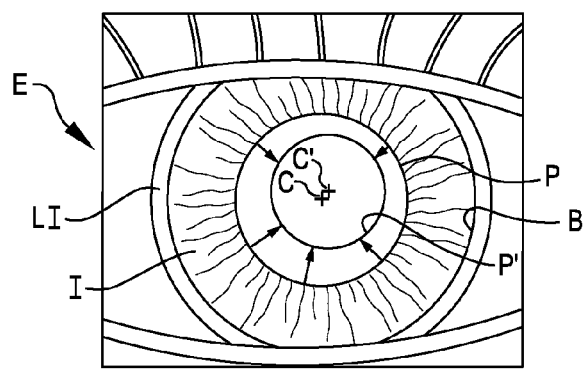
FIG. 11 is a diagram representing an eye and showing that as the pupil contracts, it also shifts in position.

As the pupil contracts, it also shifts in position. This relationship is shown in FIG. 11. Pupil P contracts and/or expands with changes in brightness or illumination, with these changes in illumination optionally including changes in the brightness of the object or target being viewed, changes in the ambient light around the viewing target, and the like.

Along with changes in the overall size of pupil P when the eye E is subjected to different viewing conditions, the location of the pupil center C may also change. It should be noted that this change in location of the pupil center may be separate from and in addition to any overall movement of the eye. In other words, even if the eye E were to remain at an overall fixed location in space so that the cornea and the retina of the eye did not move, as the pupil P contracts from a first pupil configuration P to a smaller pupil configuration P, the center C of the pupil may undergo a corresponding change in location to a new pupil center C'. This change in pupil center location is encompassed within the term "pupil center drift" as that term is used herein.

The position and size of the pupil are correlated. That is, as the pupil contracts, it shifts. So with two measurements of the pupil, it is possible to determine this correlation and describe it as a linear shift (which it will be to a good approximation). So for any known or measurement pupil size, from these two images it will be possible to determine a corresponding pupil position. In an embodiment, one of the two images is obtained from a corneal topographer. Alternative embodiments may determine the relationship of pupil size and position using additional images (such as to determine a curved relationship), by continuously or dynamically measuring location and pupil size during changes in illumination, or the like. In addition, in an embodiment, a pupil image is obtained from the corneal topographer, and that image is used to determine the relationship between the pupil size and location.

Figure 12:
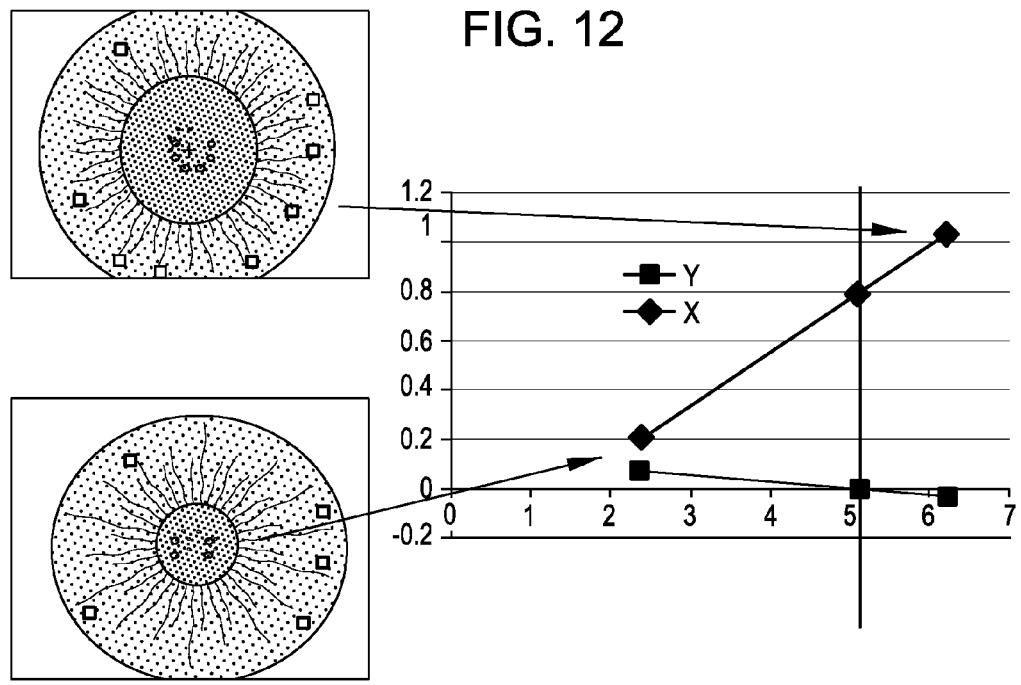
FIG. 12 schematically illustrates a relationship between pupil size and location as derived from images of the eye under scotopic/mesopic conditions and photopic conditions, and also shows determination of a wavefront sensor pupil position from a pupil size identified using wavefront aberrometry data, combined with the relationship.

Thus, with both a photopic image and a scotopic/mesopic image, a relationship may be established between pupil size and position. Thus, using the pupil size obtained in the wavefront image, it is possible to determine the pupil position when the wavefront image was acquired. To this end, the pupil position is described as a linear function of the pupil size by evaluating the pupil size and position from the scotopic/mesopic and photopic images as shown in FIG. 12. Then the corresponding pupil size calculated from the wavefront sensor image is used to "look up" the position of the pupil on this curve. This correlation correctly allows for the appropriate pupil position shift as the eye changes it shape. The offset from the center (or other reference point) of the wavefront image relative to the iris registration image can be used to provide the exact relationship between the various images, taking all the phenomena into account.

Thus, using the above, the relationship established pursuant to step 404 includes: registering the outer iris boundary information that is found in the corneal topography image with that from the iris registration image, and registering the position of the wavefront pupil to the proper position as interpolated from the iris images. These functions are performed, for example, via the registering module 90 and the relationship module 92.

During embodiments of the multi-modal eye diagnosis described herein and shown schematically in FIG. 13, data fusion is optionally achieved when the correct spatial relationship can be established between some or preferably all of the following four datasets:

1. corneal topography image, associated corneal elevation map or data derived from the image or elevation map (such as local gradients of the corneal surface)

2. wavefront image, associated reconstructed ocular wavefront or data derived from the image or wavefront reconstruction (such as the wavefront decomposition into function sets (e.g., Fourier and zonal reconstruction, and Zernike and Taylor polynomial reconstruction)

3. Scotopic eye image or data derived from the scotopic eye image (such as scotopic pupil shape, scotopic pupil size, scotopic pupil centroid position, limbus or outer iris boundary, iris pattern, blood vessel pattern, or artificial landmarks such as flap cut, intrastromal bubble)

4. Photopic eye image or data derived from the photopic eye image (such as photopic pupil shape, photopic pupil size, photopic pupil centroid position, limbus or outer iris boundary, iris pattern, blood vessel pattern, or artificial landmarks such as flap cut, intrastromal bubble)

For embodiments invention disclosed herein, as shown in FIG. 13, registering of the multiple datasets may be used in the following manner. First, the relationship between pupil position and diameter is established from the scotopic and photopic images, as shown in FIG. 12. The pupil size is measured on the wavefront image (along with the relative wavefront offset) by back illuminating the pupil by the scattering source on the retina, with the retina aperturing the aberrometry data (Detections 02 and 03, FIG. 13). Thus, the size, shape, and location of the pupil can be accurately determined. For the pupil size determined from the wavefront measurement, the relative position on the iris images is determined using the previously established relationship of size to position (FIG. 12). Note that the wavefront pupil size is not necessarily between the pupil sizes of the photopic and scotopic images, and may be smaller than the pupil in the photopic image, larger than the pupil in the scotopic image, or the same size as the pupil in either of these images. As long a relationship between size and position is established, the position of the wavefront can be determined or estimated. After the position is determined or estimated, ambiguity as to the position of the images is removed, or at least reduced, and all are thus registered correctly (Registration R2, FIG. 13).

The registration step R1 is now described. First, the iris landmarks are detected from the CT image I1. To do this step, the outer circular boundary C1 of the corneal topography spot pattern is detected. A second circular boundary C2 is chosen to include the limbus border. C1 and C2 are concentric and form a ring of iris structure. A coordinate transformation from cylindrical to Cartesian coordinates is performed—the iris structure ring is unwrapped into an iris structure strip. The iris structure strip is filtered with a Sobel y-gradient filter for edge detection followed by binarization of the image. Additional aspects of determining the center of the limbus and/or pupil may be understood with reference to U.S. Pat. No. 7,044,602 in the name of Chernyak, the full disclosure of which is incorporated herein by reference.

The same steps are performed for the photopic eye image I4. The translational offset between the two limbus centers is now known. A rotational offset between the two images I1, I4 can be computed by correlation of the two iris feature strips with iterations around scale due to elastic deformation of the iris features for constricting/dilating pupils. Thus, the photopic eye image I4 and the CT image I1 can be registered to each other.

The photopic and scotopic eye measurements are registered to each other using known methods, for example via use of iris landmarks (Registration 3). Afterwards, all images and data from the images may be fused.

While exemplary embodiments have been described herein in some detail, for clarity of understanding and by way of example, a variety of adaptations, changes, and modifications will be clear to those of skill in the art. For example, a variety of wavefront sensor systems from a variety of alternative suppliers may be employed. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method for registering optical datasets of an eye, the method comprising:
   determining a relationship between a pupil location and size based on different illumination states of the eye;
   obtaining a first optical dataset of the eye and a first associated pupil size; and
   registering the first optical dataset of the eye with a second optical dataset of the eye using the relationship.

2. The method of claim 1, wherein the relationship between pupil location and size is linear.

3. The method of claim 1, wherein determining a relationship comprises continuously or dynamically measuring location and pupil size due to changes in illumination.

4. The method of claim 1, wherein determining the relationship acquiring the plurality of images comprises obtaining scotopic and photopic optical datasets of the eye, and establishing a relationship based on pupil sizes in the images.

5. The method of claim 4, wherein the first optical dataset is derived, at least in part, from a wavefront measurement instrument; and wherein the second optical dataset is derived at least in part from a corneal topographer.

6. The method of claim 5, wherein registering comprises aperturing of the aberration data of the first dataset by the iris of the eye.

7. The method of claim 1, wherein the first optical dataset is derived, at least in part, from a wavefront measurement instrument; and wherein the second optical dataset is derived at least in part from a corneal topographer.

8. The method of claim 7, wherein registering comprises aperturing of the aberration data of the first dataset by the iris of the eye.

9. A system for registering optical datasets of an eye, the system comprising:
   a memory for storing a relationship between a pupil location and size based on different illumination states of the eye;
   an input for receiving a first optical dataset of the eye and a first associated pupil size;
   an output; and
   a processor coupled to the memory, the processor coupling the input to the output so as to register the first optical dataset of the eye with a second optical dataset of the eye using the relationship, and transmitting the registered datasets to the output.

10. The system of claim 9, wherein the relationship between pupil location and size is linear.

11. The system of claim 9, further comprising a module that may be accessed by the processor to establish the relationship between the pupil location and size.

12. The system of claim 9, further comprising a second input for receiving scotopic and photopic optical datasets of the eye, and wherein the processor couples the second input to the memory to develop the relationship.

13. The system of claim 12, wherein the first optical dataset is derived at least in part from a wavefront measurement.

14. The system of claim 13, wherein the second optical dataset is derived, at least in part, from a corneal topograph.

15. The system of claim 9, wherein the first optical dataset is derived, at least in part, from a wavefront measurement.

16. The system of claim 15, wherein the second optical dataset is derived, at least in part, from a corneal topograph.

* * * * *